(12) United States Patent
Dai

(10) Patent No.: US 11,421,281 B2
(45) Date of Patent: Aug. 23, 2022

(54) METHODS FOR IDENTIFICATION OF DRIVER MUTATIONS IN A PATIENT TUMOR BY MUTATION PROCESSING BASED RECONSTRUCTION OF TUMOR DEVELOPMENTAL HISTORY

(71) Applicant: UNIVERSITY OF IOWA RESEARCH FOUNDATION, Iowa City, IA (US)

(72) Inventor: Donghai Dai, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 301 days.

(21) Appl. No.: 16/484,772

(22) PCT Filed: Feb. 23, 2018

(86) PCT No.: PCT/US2018/019436
§ 371 (c)(1),
(2) Date: Aug. 8, 2019

(87) PCT Pub. No.: WO2018/156904
PCT Pub. Date: Aug. 30, 2018

(65) Prior Publication Data
US 2019/0367993 A1    Dec. 5, 2019

Related U.S. Application Data

(60) Provisional application No. 62/462,739, filed on Feb. 23, 2017.

(51) Int. Cl.
*C12Q 1/6806* (2018.01)
*C12Q 1/6886* (2018.01)

(52) U.S. Cl.
CPC ......... *C12Q 1/6886* (2013.01); *C12Q 1/6806* (2013.01)

(58) Field of Classification Search
CPC ................ C12Q 1/6806; C12Q 1/6886; C12Q 2535/122; C12Q 2563/179
See application file for complete search history.

(56) References Cited

U.S. PATENT DOCUMENTS

2016/0341731 A1    11/2016  Sood et al.
2019/0249261 A1*   8/2019   Dingli ................. C12Q 1/6827

FOREIGN PATENT DOCUMENTS

WO    WO-2016048952 A1 *  3/2016  ........... C12Q 1/6886
WO    2016090273 A1       6/2016

OTHER PUBLICATIONS

Wu et al. Evolution and heterogeneity of non-hereditary colorectal cancer revealed by single-cell exome sequencing. Dec. 12, 2016, Oncogene, 36, pp. 2857-2867 (Year: 2016).*
Khattra. Charting clonal heterogeneity in breast cancers : from bulk tumor genomes to single-cell genotypes. May 2015. University of British Columbia. (Year: 2015).*
Gawad et al. Dissecting the clonal origins of childhood acute lymphoblastic leukemia by single-cell genomics. Dec. 16, 2014. PNAS, 111, 50, pp. 17947-17952. (Year: 2014).*
Gawad supplemental information, obtained at https://www.pnas.org/content/pnas/suppl/2014/11/25/1420822111.DCSupplemental/pnas.1420822111.sapp.pdf (Year: 2014).*
Wu Supplementary Table S1 obtained at https://www.nature.com/articles/onc2016438#MOESM33 (Year: 2016).*
American Cancer Society , ACS Cancer Facts and Figures, 56 pages (2015).
Deshwar, A , et al., "PhyloWGS: reconstructing subclonal composition and evolution from whole-genome sequencing of tumors", Genome Biol 16, 35, 20 pages (2015).
El-Kebir, M , et al., "Reconstruction of clonal trees and tumor composition from multi-sample sequencing data", Bioinformatics 31(12), i62-i70 (2015).
Hajirasouliha, I , et al., "A combinatorial approach for analyzing intra-tumor heterogeneity from high-throughput sequencing data", Bioinformatics 30(12), i78-i86 (2014).
Jiao, W , et al., "Inferring clonal evolution of tumors from single nucleotide somatic mutations", BMC Bioinformatics 15, 35 (2014).
Kandoth, C , et al., "Mutational landscape and significance across 12 major cancer types", Nature 502, 333-339 (2013).
Miller, C , et al., "SciClone: inferring clonal architecture and tracking the spatial and temporal patterns of tumor evolution", PLOS Comput Biol 10(8), e1003665 (2014).
Oesper, L , "Quantifying tumor heterogeneity in whole-genome and whole-exome sequencing data", Bioinformatics 30(24), 3532-3540 (2014).
Oesper, L , et al., "THetA: inferring intra-tumor heterogeneity from high-throughput DNA sequencing data", Genome Biol 14, R80, 21 pages (2013).
Patent Cooperation Treaty , International Searching Authority, Search Report and Written Opinion for PCT/US2018/019436, 11 pages, dated Jul. 10, 2018.
Roth, A , et al., "PyClone: statistical inference of clonal population structure in cancer", Nat Methods 11(4), 396-398 (2014).
Tokheim, C , et al., "Evaluating the evaluation of cancer driver genes", PNAS 113, 14330-14335 (2016).
Zhang, J , et al., "Development of TEAPOT Algorithm to Reconstruct Individual Ovarian Tumors' Evolutionary History", Presentation at American Association of Cancer Research annual meeting in 2018.
Zhang, J , et al., "Development of TEAPOT algorithm to reconstruct individual ovarian tumors' evolutionary history based upon bulk and single cell whole exome sequencing data", Cancer Research, Abstract 219, Proceedings: AACR Annual Meeting, Chicago, IL, Apr. 14-18, 2018.

* cited by examiner

*Primary Examiner* — David C Thomas
(74) *Attorney, Agent, or Firm* — Viksnins Harris Padys Malen LLP

(57) ABSTRACT

In certain embodiments, the present invention provides a method to identify driver mutations in a tumor and its cancer cell subpopulations. The method of the present invention is used to design treatment strategies for cancer patients.

15 Claims, 8 Drawing Sheets

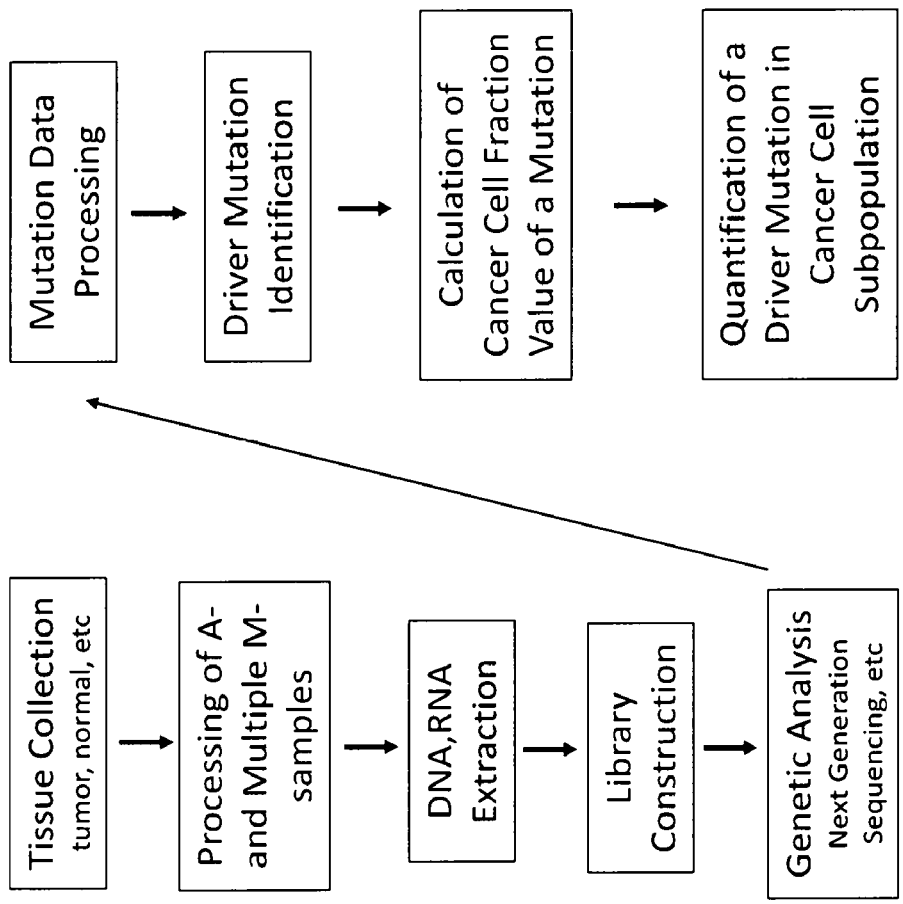
Fig. 1. An Overall Experimental Flowchart

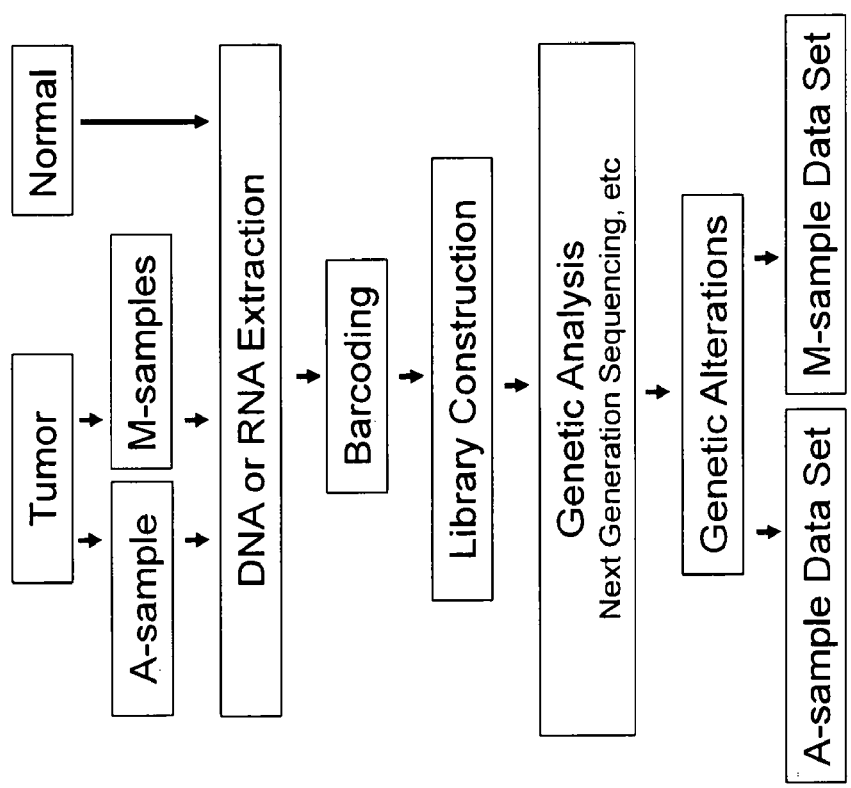

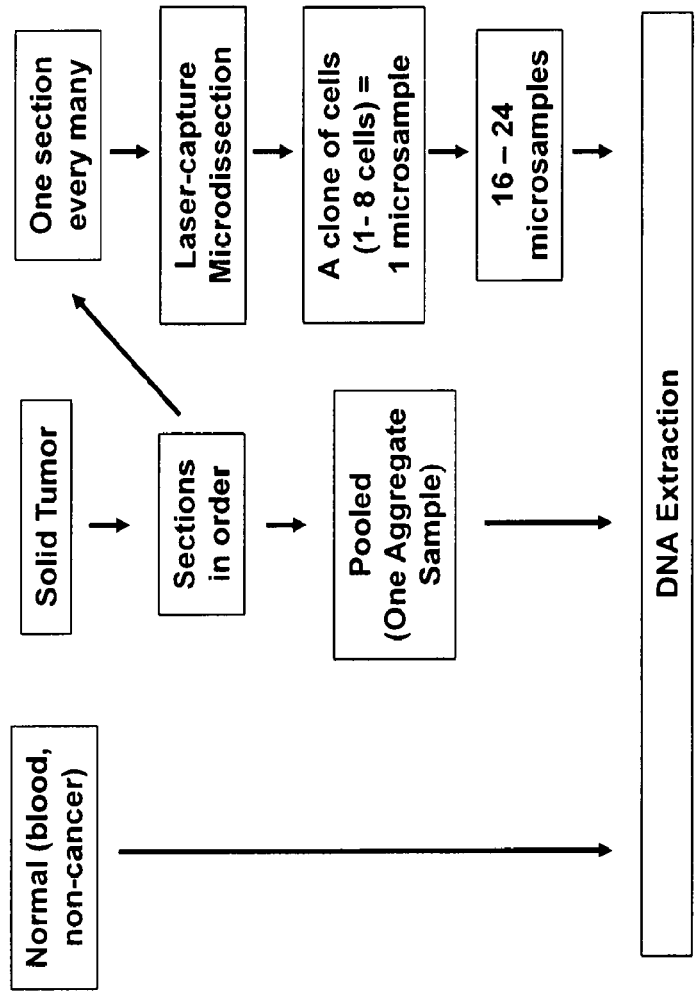
Fig. 3. Acquisition of Aggregate- and Micro-samples

Fig. 4. Laser Captured Microdissection of a Small Clone of Cells
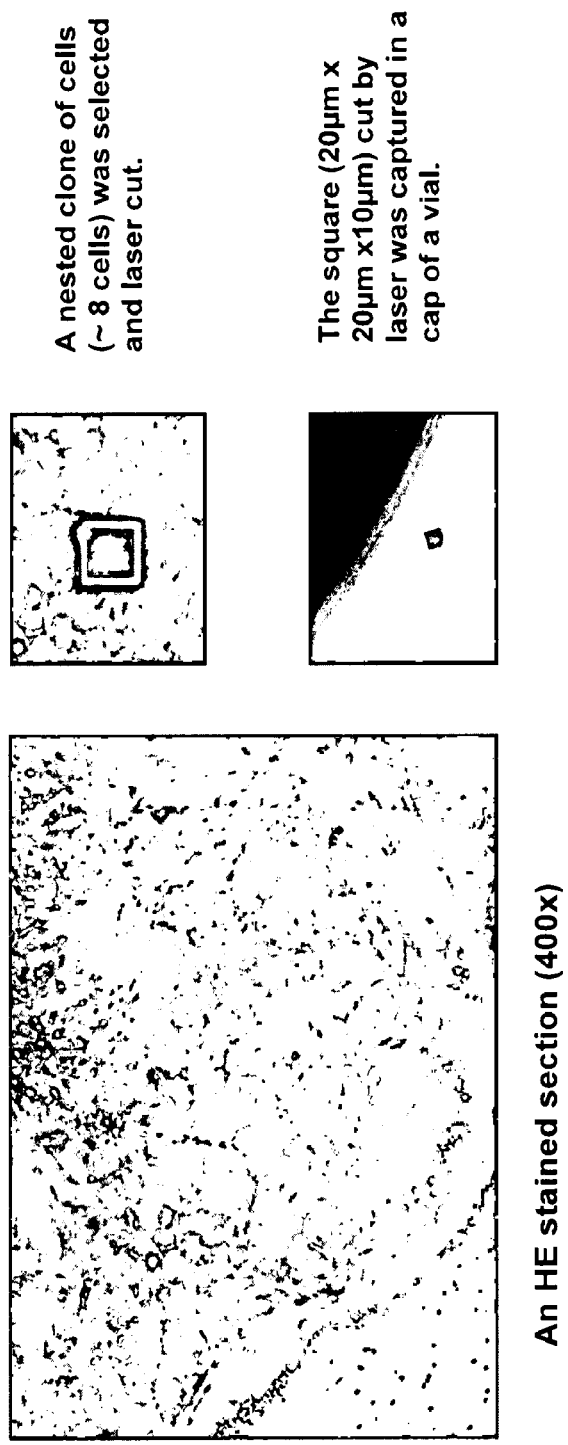

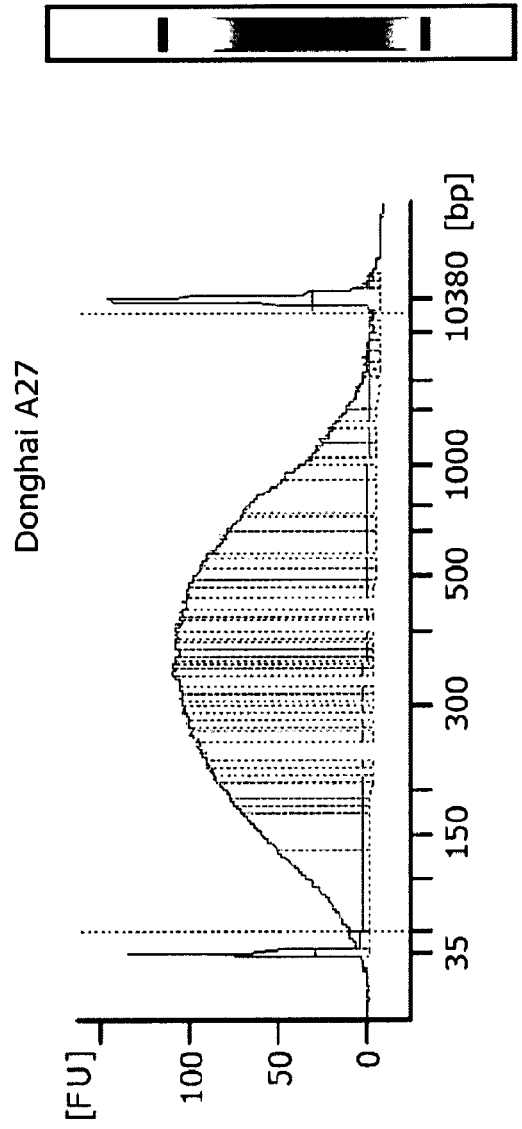
Fig. 5. DNA Fragments after Shearing from an A-sample by High Sensitivity DNA Assay

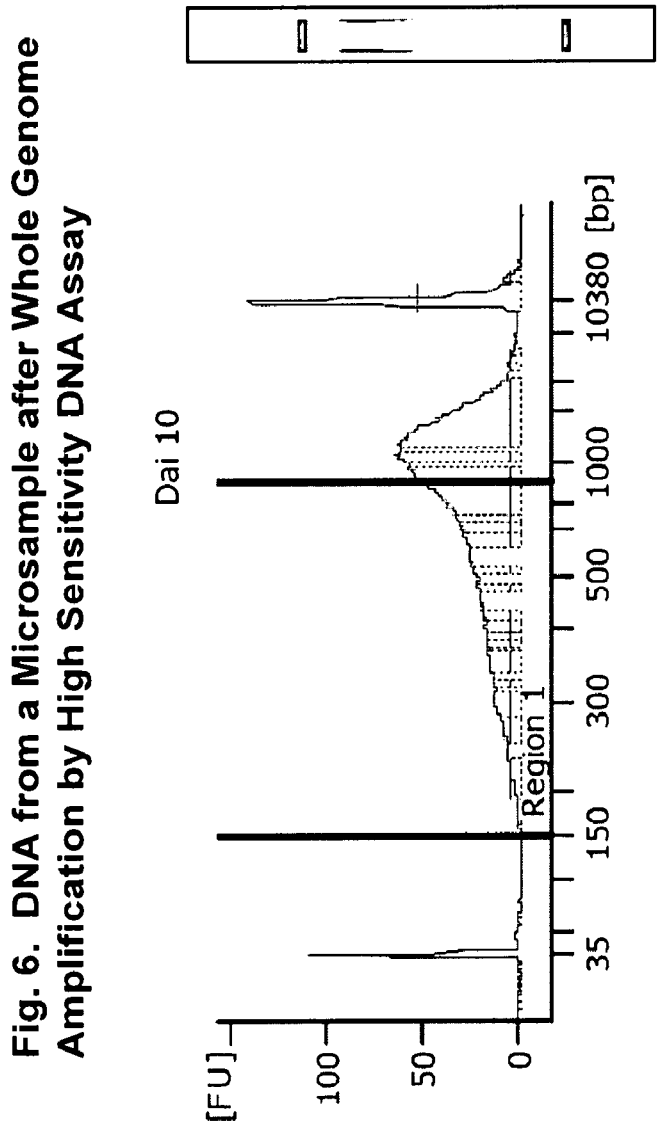
Fig. 6. DNA from a Microsample after Whole Genome Amplification by High Sensitivity DNA Assay

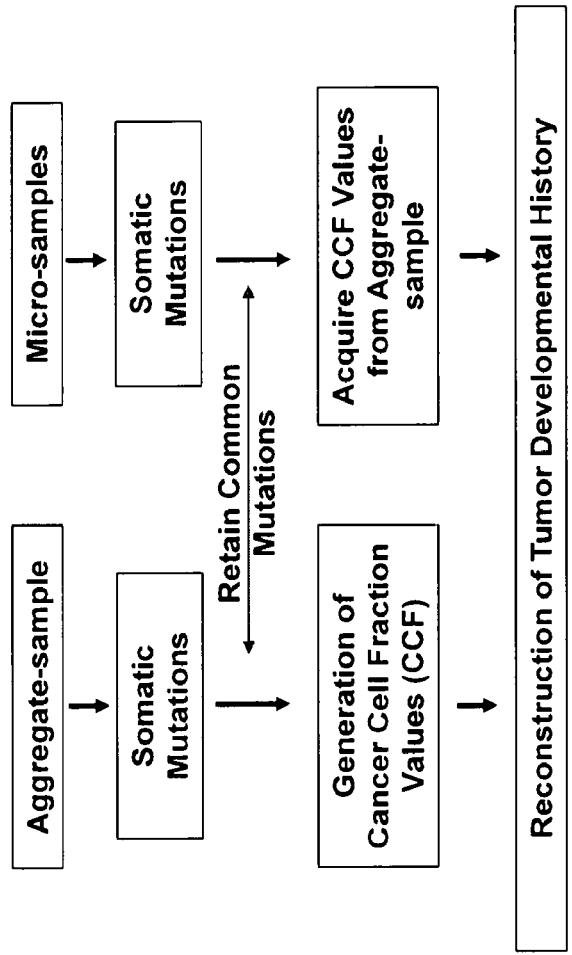

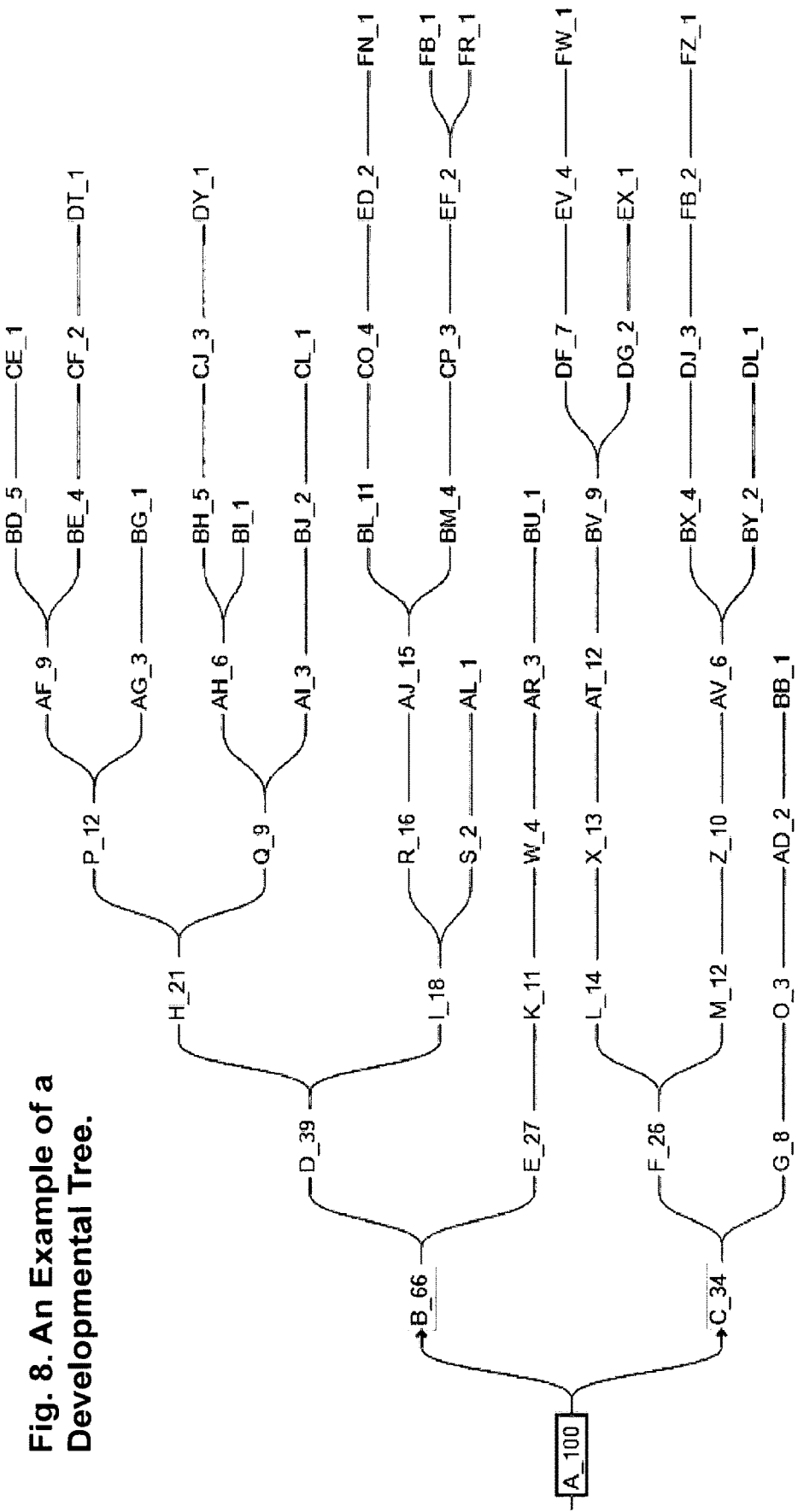
Fig. 8. An Example of a Developmental Tree.

METHODS FOR IDENTIFICATION OF DRIVER MUTATIONS IN A PATIENT TUMOR BY MUTATION PROCESSING BASED RECONSTRUCTION OF TUMOR DEVELOPMENTAL HISTORY

RELATED APPLICATION

This application claims the benefit of priority of U.S. Provisional Application Ser. No. 62/462,739 filed on Feb. 23, 2017, which application is incorporated by reference herein.

BACKGROUND OF THE INVENTION

Despite tremendous efforts made to conquer cancer in the past decades, overall cancer mortality remains high and has not changed substantially (ACS (2017) Cancer Facts and Figures. American Cancer Society). The US has identified personalized precision medicine as a national priority and launched a $215 million precision medicine initiative in 2015. The Cancer Moonshot initiative added more urgency and momentum to develop innovative approaches and cure cancer.

Identification of driver mutations in a tumor as therapeutic targets is seen as a critical step for precision medicine in cancer and is necessary for cure of cancer. A true driver mutation should be defined by the role of a mutation in tumor evolution in an individual patient. The true driver mutation within a gene confers a selective growth advantage (promoting cancer cell growth) in its host cells under the tumor's microenvironment (Tokheim C J et Proc Natl Acad Sci USA 2016, 113: 14330). However, there is no methods available currently that will assay the growth promoting effect of a mutation in patient tumor. Current arts use driver mutations to refer those mutations in cancer genes that are important in cellular functions and supported with indirect evidence of cancer promoting effect. Many driver mutations have thus been identified in the past decades. For instance, recently Kandoth et al. reported 127 driver mutations as the result of The Cancer Genome Atlas, a national project to decode cancer that has enrolled more than 7000 cases across 12 types of human cancer at the time of report (Kandoth, C., et al. *Nature* 2013, 502, 333-339). Those driver mutations, however, were identified largely based on two criteria: (1) these mutations occur frequently in human tumors, and (2) the mutations are proven to be biologically important in in vitro, animal studies and clinical observations in aggregated data. Their role in tumor progression, however, has not been directly examined and validated in individual patients. Application of the knowledge of driver mutations has yet to translate into discovery of effective treatments and substantial improvement in cancer survival, but unfortunately, this current paradigm remains the prevailing approach. For instance, one of the most popular methods to identify driver mutations to guide treatment is through the test kit offered by Foundation Medicine (www.foundationmedicine.com). The Foundation One kit for all solid tumors has a panel of 315 genes and select introns from 28 genes. Known mutations in these genes will be designated as driver mutations and will be recommended as therapeutic targets for intervention if there is a drug available. However, current targeted therapies are ineffective for most solid tumors and treatment can only bring limited benefit without influencing high cancer mortality as whole.

There are two major flaws in these approaches: (1) they are not a humanized approach: a gene function is not determined in vivo in a human where its function is the consequence of genetic context and interaction with tumor microenvironment; and (2) they are not a personalized approach for an individual patient, since importance of a gene is pre-determined without considering the patient's other mutations (mutational context). Additionally, it is well established that there is intra-tumor heterogeneity, where a tumor may harbor different subpopulations that are driven by different driver mutations.

A mutation's effect in tumor progression and intra-tumor heterogeneity can only be fully understood with appreciation of tumor developmental history. While research to understand tumor heterogeneity and identify driver mutations has been an ongoing endeavor for decades, efforts in this field through informatical approaches have produced some exciting preliminary findings. The prior works include the following algorithms, PyClone (Roth, A., et al. *Nat. Methods* 2014, 11, 396-398), ThetA (Oesper, L., et al. *Genome Biol.* 2013, 14, R80; and Oesper, L., *Bioinformatics.* 2.14, 30, 3532-3540), SciClone (Miller, C. A., et al. *PLoS. Comput. Biol.* 2014, 10, e1003665), AVDPM (Hajirasouliha, I., et al. *Bioinformatics.* 2.14, 30, i78-i86), Phylosub (Jiao, W., et al. *BMC. Bioinformatics.* 2014, 15, 35) and PhyloWGS (Deshwar, A. G., et al. *Genome Biol.* 2015, 16, 35) and other algorithms. They have been proposed to infer intra-tumor heterogeneity and cluster mutations based on next generation sequencing data. These algorithms have produced some results that are primitive to understand tumor evolution. Their clusters could not be directly translated into biological concept of subclones with clear lineages. Due to some limitations in the design of these methods, they will not be able to expand their work further to describe tumor evolution in chronological detail and assess the role of a genetic mutation in tumor evolution.

Identification of mutations influential in the development of a tumor is particularly important to design a treatment strategy. This can only be done with reconstruction of a more comprehensive tumor developmental history. Without multiple sampling from a tumor specimen, these methods are not able to establish any meaningful tumor developmental history. El-Kebir et al. has introduced a method using multiple samples for reconstruction of clonal trees (El-Kebir, M., et al. *Bioinformatics.* 2015, 31, i62-i70), representing a novel direction to study tumor evolution. However, their individual sample size was too big to have a pure clone in each sample, which directly contradicts the clone concept in their mathematical model and their statistical methods have resulted in the loss of lineage relationship that they struggled to build. Their method has failed to produce a significant developmental tree that could be used to understand tumor evolution.

Accordingly, a new method to identify mutations influential in the development of a tumor in a patient tumor is needed.

SUMMARY

In certain embodiments, the present invention provides a method of acquiring specimens that are representative of a tumor in a patient comprising:
  (a) obtaining biological samples from the patient, wherein the samples include:
    (i) a sample of a tumor mass,
    (ii) a sample from non-cancerous tissue;
  (b) collecting more than one micro-sample (M-sample) from the tumor mass, wherein each M-sample comprises one to 100 cells that are clonally related; and (c) converting the tumor mass after the M-samples are collected into an aggregate sample (A-sample).

In certain embodiments, the one or more M-sample collected as a single cancer cell or as a small number of cancer cells from an individual tumor section or from a fine needle biopsy.

In certain embodiments, the one or more M-sample is obtained from the tumor mass as a cell suspension by means of enzymatic digestion or mechanical disruption.

In certain embodiments, the sample is fresh tissue, snap frozen samples, formalin-fixed paraffin embedded specimens, or collected by other methods that reasonably preserve quality of genome DNA or RNA.

In certain embodiments, the tumor is a primary tumor.

In certain embodiments, the tumor is a metastatic tumor.

In certain embodiments, the tumor is a solid tumor, such as breast, colon, lung, or prostate cancers, as well as blood cancers such as leukemia or multiple myeloma.

In certain embodiments, the non-cancerous tissue is any non-cancerous tissue from the same patient, such as blood or a normal tissue from the adjacent tissue or from different organs.

In certain embodiments, the DNA from the one or more M-samples is individually amplified by means of whole genome amplification.

In certain embodiments, the method further comprises (d) shearing the DNA from the one or more M-samples, the A-sample, and sample from non-cancerous tissue.

In certain embodiments, the method further comprises (e) barcoding the DNA.

In certain embodiments, the method further comprises (f) exon capturing the barcoded DNA from the A-sample, the barcoded DNA from the non-cancerous tissue, and from the one or more M-samples.

In certain embodiments, the method further comprises performing next generation sequencing of the A-sample either on the barcoded DNA (e.g., step (e)), or exon-captured barcoded DNA (e.g., step (f)), of the non-cancerous tissue sample, and of the one or more M-samples to generate DNA sequencing data for the A-sample, the non-cancerous tissue sample, and the one or more M-samples.

In certain embodiments, the present invention comprises a method of creating a tumor developmental history comprising:
 (a) obtaining the DNA sequencing data for an A-sample, a non-cancerous tissue sample, and one or more M-samples;
 (b) comparing the DNA sequencing data between the A-sample and the non-cancerous tissue sample to determine mutations specific for the A-sample;
 (c) comparing the DNA sequencing data between the A-sample and each of the one or more M-samples to determine which mutations are unique for the M-samples, and which mutations are common to the A-sample;
 (d) calculating the cancer cell fraction (CCF) value for each mutation in the A-sample;
 (e) assigning a CCF value to each mutation common between the A-sample and an M-sample; and
 (f) constructing the tumor developmental history,
wherein a mutation common to the A-sample and all M-samples is a driver mutation.

In certain embodiments, the present invention comprises a method of treating a patient having a driver mutation identified using the method described herein, the method of treating comprising administering a therapeutic agent that targets cells comprising the driver mutation.

In certain embodiments, the present invention provides a method to identify driver mutations cells in a tumor based on a tumor developmental history. The mutations are identified based on their role in patient tumor growth and are recognized as the direct drug target to guide selections of the most effective targeted agents for anti-cancer treatment. The present invention describes a method that includes several experimental and analytical procedures (FIG. 1): (1) a method to collect normal and tumor specimens; (2) processing of A- and multiple M-samples; (3) extraction of DNA and/or RNA; (4) library construction for genetic analysis; (5) next generation sequencing and other genetic analyses; (6) mutation data processing; (7) driver mutation identification; (8) calculation of cancer cell fraction value for a mutation; (9) quantification of a driver mutation in cancer cell subpopulation. This method has been detailed and it is feasible as illustrated at FIG. 1. It has offered a solution for the most critical question in cancer treatment: identification of drug targets. It has addressed the issue of intra-tumor heterogeneity that is essential for personalized precision cancer medicine: (1) it quantifies the percentage of cancer cells carrying a driver mutation in a tumor; (2) it provides information to design a therapy targeting multiple driver mutations simultaneously. This method can be used in hospitals and clinics as well as diagnostics laboratories for the purpose to assist cancer patient management and design treatment strategy. A full implementation of this method will substantially improve treatment efficacy and reduce cancer mortality and morbidity.

BRIEF DESCRIPTION OF DRAWINGS

FIG. 1 shows an overall experimental flowchart.

FIG. 2 shows tissue processing and genetic data generation.

FIG. 3 shows acquisition of micro-samples (M-samples) and aggregate-samples (A-samples).

FIG. 4. Laser captured microdissection of a small clone of cells. The left panel shows a HE stained section (400×). The upper right panel shows a nested clone of cells (~8 cells) that was selected and laser cut. The lower right panel shows the square (20 µm×20 µm×10 µm) cut by laser that was captured in a cap of a vial.

FIG. 5. DNA fragments after shearing from an A-sample by high sensitivity DNA assay.

FIG. 6. DNA from a microsample (M-sample) after whole genome amplification by high sensitivity DNA assay.

FIG. 7. Acquisition of data sets from aggregate-sample (A-sample) and micro-samples (M-samples).

FIG. 8 shows an example of a developmental tree.

DETAILED DESCRIPTION

In certain embodiments, the present invention provides methods of acquiring cancer cell specimens from a patient, processing mutation data for reconstruction of the patient's tumor developmental history, and identifying driver mutations in cancer cell subpopulations from the patient's tumor. This method has also presented inventions to identify the driver mutations in an individual patient tumor through reconstruction of tumor developmental history.

Specimen Acquisition

In order to reconstruct a tumor's developmental history, tissue acquisition is an important first step. The specimens need to represent a tumor in evolution and reasonably sufficient genetic information needs to be determined so that reconstruction of tumor developmental history can be performed. Collection of a tumor tissue specimen that is representative of the disease in the patient is important in order to reconstruct the tumor's history. Every micro-sample, regardless of the cell number it contains, is close in lineage proximity and is a unique unit to function as a "leaf" in the reconstructed developmental "tree." The entire collection of micro-samples is representative of the tumor tissue being studied.

Specimen Collection

First, specimens are obtained from a tumor mass and from normal tissue (i.e., control) from a cancer patient. In certain embodiments, the tumor tissues are sampled from a single primary site, if there is only a single tumor in the patient. In certain embodiments, tumor tissues are sampled from different locations in the patient when cancer has spread, and presents as a disease with multiple (e.g., metastatic) lesions. In order for specimens to be representative of a tumor mass (or the entire disease), a sufficient volume and/or number of samples should be collected from tumor masses in all of the lesions. The collected tumor tissue sample(s) for the subsequent analysis is called the "tumor specimen". For example, an entire primary tumor is removed from a tissue or organ, so that the entire primary tumor is the tumor specimen for the primary tumor. The specimen collected from a metastatic lesion is a tumor specimen representing the metastatic lesion. The tumor specimens from the primary site and all metastatic lesions are the tumor specimen representing the disease (cancer) in the patient. In certain embodiments, normal tissue is also collected from the same patient and is used as the reference (control) for the detection of somatic mutations. In certain embodiments, normal tissue is a sample of non-cancer tissue from the same or different organ removed during a surgery, from a biopsy, or from blood collected from the patient. In certain embodiments, the normal and tumor specimens are fresh tissue, snap frozen samples, formalin-fixed paraffin embedded specimens, or collected by other methods that reasonably preserve quality of genome DNA or RNA.

For the purposes of determining the tumor heterogeneity and cancer developmental history of a tumor specimen, in certain embodiments, multiple microsamples (M-samples) are collected to represent a tumor specimen. In certain embodiments, each M-sample contains one to several dozens of cancer cells, depending upon representation of clonal purity needed for a study. In certain embodiments, the M-sample comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 cells. While a single cancer cell represents the purest clonality, it may not yield its entire genomic DNA for sequencing, due to loss in the processing and amplification. As used herein the term "clonally related" means that the cells are derived directly or indirectly from a single cell of origin, and/or are daughter cells arising from a single cell. Therefore, an M-sample with a few to several dozen cancer cells that are close in clonality may offer significantly better DNA for genome sequencing and retain the clonality for the group of cells. In certain embodiments, an M-sample is acquired as a single cancer cell or a small number of cancer cells from an individual tumor region or from a fine needle biopsy. Alternatively, in certain embodiments, enzymatic digestion or mechanical methods are used to create cell suspension, if the obtained cells can reasonably represent the entire tumor specimen.

In certain embodiments, after collection of multiple M-samples from a tumor specimen, all the remaining cancer cells in the tumor specimen are collected and called the "aggregate sample" (A-sample) of the tumor. Therefore, the original tumor specimen is converted into a single A-sample and multiple M-samples. Both the M-samples and the A-sample are important for the generation of two sets of genetic data in order to reconstruct the tumor's developmental history.

In certain embodiments, an individual metastatic lesion is treated as a single tumor specimen, similarly as a tumor specimen for the primary lesion. As used herein, the term "primary tumor" is a tumor that is at the original site where it first arose. For example, a primary brain tumor is one that arose in the brain as opposed to one that arose elsewhere and metastasized (spread) to the brain. In this embodiment, an A-sample and multiple M-samples are created to study the developmental history of the tumor specimen of the metastatic tumor.

DNA Sample Analysis

After the control is collected and the A-sample is processed, the DNA from the samples is extracted. In certain embodiments, the DNA is extracted using QIAGEN DNeasy Blood & Tissue Kit. Alternatively, DNA can be extracted by other commercially methods as well. In certain embodiments, the genomic DNA is then sheared (e.g., by using a Covaris sonicator E220) to yield medium size of approximately 300 bp. Alternatively, other methods that break down the size of a DNA to smaller fragments for sequencing efficiency can be used. The sheared (i.e., fragmented) DNA is "barcoded" (e.g., by using the Rubicon ThruPLEX kit (Takara Bio USA) with dual indexes). Other methods that add adaptors that distinguish individual DNA samples can also be used. In certain embodiments, the barcoded DNA is analyzed (e.g., by using an Agilent Bioanalyzer High Sensitivity DNA assay and other methods that ensure the quality of DNA for next step).

In certain embodiments, each of M-samples are individually amplified by means of whole genome amplification using PicoPLEX DNA-seq kits (Takara Bio USA). In certain embodiments, exon capture is performed on the sheared and barcoded DNA from the A-sample, from the matched normal (tissue or blood), and from the individually amplified M-samples (e.g., using xGen Exome Research Panel from IDT). Next generation sequencing was then performed on the DNA libraries (e.g., using an Illumina NextSeq sequencer). Other sequencing machines, such as Illumina MiSeq, HighSeq and NovoSeq etc. can also be used.

Creation of Data Sets

In certain embodiments, somatic mutation data sets are established for reconstruction of tumor developmental history. Using the method described above and in Example 2, an A-sample and multiple M-samples are generated from a tumor specimen, and then nucleic acid sequencing data are generated. The DNA sequencing results for the somatic mutations in the A-sample and M-samples are analyzed using bioinformatics tools. In certain embodiments, a variant is filtered out based on its sequencing quality, total reads and alternative reads for the consistency with sequencing design and workflow. Copy number for a segment that covers a mutation can be calculated by many algorithms including Varscan 2 (Koboldt, D., Zhang, Q., Larson, D., Shen, D., McLellan, M., Lin, L., Miller, C., Mardis, E., Ding, L., & Wilson, R. (2012). VarScan 2: Somatic mutation and copy number alteration discovery in cancer by exome sequencing Genome Research DOI: 10.1101/gr.129684.111). Tumor purity for a tumor specimen can be estimated using many algorithms including PyLOH (Li Y, Xie X 2014 Deconvolving tumor purity and ploidy by integrating copy number alterations and loss of heterozygosity. Bioinformatics 31(4): 618).

In certain embodiments, mutation data from the A-sample and multiple M-samples generated from a tumor are created and used for reconstruction of the tumor specimen's developmental history using the following process (FIG. 7):

1. The list of somatic mutations for an A-sample is generated and called "A-sample data." The list of all mutations for an M-sample is generated and is called "M-sample data." All M-sample data are collectively called "M-sample data set."
2. The common mutations between A-sample data and M-sample data set are retained in the A-sample data and M-sample data set. All other somatic mutations in an M-sample are considered unique for the M-sample.
3. The cancer cell fraction (CCF) value for each mutation in the A-sample data is calculated using the following formulas, modified from the method of Bolli et al. (Bolli et al. 2014 Heterogeneity of genomic evolution and mutational profiles in multiple myeloma. Nat Commun 5:2997, PMID: 24429703 PMCID: PMC3905727 DOI: 10.1038/ncomms3997):

$$CCF = VAF/(\text{Tumor purity})*[\text{Tumor purity}*\text{copy number}+2*(1-\text{tumor purity})]*100\%$$

The CCF value is assigned to every common mutation at an M-sample. The CCF value for each somatic mutation estimates the fraction of cancer cells in a tumor specimen that carry the mutation.

4. The somatic mutation information from both the M-sample and A-sample data sets are used together for construction of tumor developmental history.

Quantitative Interpretation of Driver Mutations in Cancer Subpopulations Based on Reconstructed Tumor Developmental Tree In certain embodiments, a reconstructed tumor developmental history in the form of a developmental tree shows the history of cancer cells dividing to produce their next generation (FIG. 7). Letters, such as A and B, are used to represent any unique mutations. The number following a letter estimates the size of descendants. The tumor developmental tree is expressed as a rooted and bifurcated tree with nodes and edges. Somatic mutations are located at the nodes and edges.

In this example, the tumor developmental history/tree is interpreted as follows:

1. According to the tree, the "A" mutation originally occurs at a cell producing 100% of cancer cell population in the A-sample. The cell in which the "A" mutation initially occurs produces two cells that are ancestors of two subpopulations with 66% and 34% of total populations and mutations "B" and "C" originally occur.
2. A mutation's CCF value indicates the percentage of cancer cells carrying the mutation. Its location in a node specifies a progenitor cell that is the most recent ancestor cell for all cancer cells carrying the mutation.
3. The location of a mutation in a developmental tree indicates if a mutation is common or exclusive to another mutation in cancer cell subpopulations. For instance, the cells with "B" and "C" mutations are mutually exclusive. Mutation "A" is common to all cancer cells. Mutation "B" is common to all cells that carry mutation "D" or "E".
4. "Driver mutations" are non-synonymous somatic mutations in the Cancer Gene Census database (http://cancer.sanger.ac.uk/census). A non-synonymous mutation is a nucleotide substitution that alters the amino acid sequence of a protein. The definition of a true "driver mutation" is based on its role in tumor growth where a mutation confers its host cell a growth advantage. However, there is no method that can be used to assay a mutation's role in human tumor. Therefore, the prior art uses a practical method to define a "driver mutation" as a mutation occurs in a cancer gene and results in a functional consequence in a cell based on aggregate and historic data. Cancer Gene Census database has listed cancer genes. Other lists do exist as well such as TCGA (https://cancergenome.nih.gov/) among others. Targeting B or C alone may not control tumor growth because either of them are present in only portion of cancer cell population, 66% and 34%, respectively. Although targeting B may be more effective than targeting C alone, design of cocktail therapy targeting both mutations potentially would be more effective in treating the tumor than administering a single agent against one of the growth advantageous mutations.

Aspects of the Invention

In one embodiment, a reverse mitosis procedure comprises:
1) Finding a sister cell for a single cell;
2) Finding the parent cell for the single cell and its sister cell from step 1); and
3) Repeating steps 1) and 2) to find the sister cell and the parent cell for the parent cell identified from step 2) until the ancestor cell is found.

The invention will now be illustrated by the following non-limiting Examples.

EXAMPLE 1

In certain embodiments, the method of invention comprises the following steps:
1) The innovative method of simultaneous collection of multiple micro-samples (M-sample) and an aggregate sample (A-sample) (FIG. 3);
2) Generation of A-sample Data and M-sample data set (FIG. 7);
3) Quantitative interpretation of driver mutations in cancer subpopulations based on a tumor developmental tree;

A stepwise description of the method is given here.

Acquisition of a Human Tumor Specimen and Processing for Creation of Aggregate-Sample (A-Sample) and Multiple Micro-Samples (M-Samples).

A fresh primary tumor was acquired from an ovarian cancer patient at time of surgery. The normal tissue was from adjacent non-cancer tissue. Acquisition of micro-samples were obtained as illustrated in FIG. 3.

Briefly, the solid tumor was removed from the patient, and was sectioned. The tumor specimen had a size of approximately 5 mm×5 mm×5 mm. It was embedded in Optimal Cutting Temperature compound (OCT) and was cut into >300 sections at 10 μm thickness in a cryostat. One section was selected every 20 sections following the order of the sectioning process. The sections were processed by hematoxylin and eosin staining (HE staining). FIG. 4. A "nest" of cells appearing to be clonal was identified. Using a Leica LMD7000 system at Central Microscopy Research Facility at the University of Iowa, an "area under microscope" of approximately 1000 $\mu m^2$ was selected that yielded a square of approximately 400 $\mu m^2$ after laser cutting. This square contained approximately 6-8 cells. The square was deposited in the cap of a 0.5 ml tube. This was one "M-sample" acquired by Laser Captured Microdissection (LCM). Sixteen squares were captured from 16 different sections of the tumor. The selection of a group of cancer cells in one M-sample appeared to be clonal based on the histology and morphology, and 16 M-samples were spaced distantly to each other to cover the entire tumor specimen.

The tumor sections after LCM capture and all other sections that were not used for LCM were pooled for DNA extraction as the "A-sample" for the tumor specimen. After the samples were washed with PBS to remove OCT, the DNA was extracted using QIAGEN DNeasy Blood & Tissue Kit. The genomic DNA was sheared by Covaris sonicator E220 to yield medium size of approximately 300 bp. The sheared (i.e., fragmented) DNA was "barcoded" using the Rubicon ThruPLEX kit (Takara Bio USA) with dual indexes. The barcoded DNA was analyzed using the Agilent Bioanalyzer High Sensitivity DNA assay, and the results are shown in FIG. 5.

The normal control was processed similarly (i.e., DNA was extracted using QIAGEN Dneasy Blood & Tissue Kit; the genomic DNA was sheared by Covaris sonicator E220 to yield medium size of approximately 300 bp; the DNA was barcoded with Rubicon ThruPLEX kit (Takara Bio USA) with dual indexes; and the barcoded DNA was analyzed using the Agilent Bioanalyzer High Sensitivity DNA assay.).

Each of 16 M-samples were individually amplified by means of whole genome amplification using PicoPLEX DNA-seq kit (Takara Bio USA). The results of the output DNA from the M-samples assayed using Agilent Bioanalyzer are provided in FIG. 6.

Exon capture was performed on the sheared and barcoded DNA from the A-sample, from the matched normal, and from the individually amplified 16 M-samples using xGen Exome Research Panel from IDT following the manufacturer's protocol (Hybridization capture of DNA libraries using xGen Lockdown Probes and Reagents, Integrated DNA Technologies, Coralville, Iowa). Next generation sequencing was then performed on the DNA libraries using an Ilumina NextSeq sequencer.

Creation of Two Somatic Mutation Data Sets for Reconstruction of Tumor Developmental History Somatic mutation data from A-sample and from 16 M-samples from the cancer patient discussed above were analyzed. High throughput sequencing was performed using an Illumina NextSeq sequencer and output Fastq was converted into a Sequence Alignment Map (SAM) file using (Burrows-Wheeler Aligner (BWA). The SAMtool was used to create sorted BAM. A BAM file (*.bam) is the compressed binary version of a SAM file. Pi Varscan 2 performed pileup and output variant call format (vcf) file for variant calling. Pileup format is a text-based format for summarizing the base calls of aligned reads to a reference sequence. The vcf specifies the format of a text file used in bioinformatics for storing gene sequence variations.

The union of all unique somatic mutations in the 16 M-samples form a set of mutations in M-samples. All mutations in this set that are also present in A-sample are retained and those mutations that either only in the A-sample or M-samples are considered unique mutations in individual samples.

For the A-sample, the copy number for each mutation was obtained using Varscan 2 (Koboldt, D., Zhang, Q., Larson, D., Shen, D., McLellan, M., Lin, L., Miller, C., Mardis, E., Ding, L., & Wilson, R. (2012)). Tumor purity of the tumor specimen was acquired using PyLOH method (((Li Y, Xie X 2014 Deconvolving tumor purity and ploidy by integrating copy number alterations and loss of heterozygosity. Bioinformatics 31(4):618. PMID: 24695406 DOI: 10.1093/bioinformatics/btu174). The cancer cell fraction (CCF) value for each mutation was calculated using the following formulas, modified from the method (Bolli et al 2014 Heterogeneity of genomic evolution and mutational profiles in multiple myeloma. Nat Commun 5:2997):

$$CCF = VAF \frac{1}{\text{Tumor purity}} [\text{Tumor purity} * \text{copy number} + 2(1 - \text{tumor purity})] * 100\%$$

VAF is the variant allele frequency value here for a specific mutation.

CCF for each mutation was then created in A-sample data. CCF is an estimate of percentage of cancer cells in the tumor specimen.

All mutations at M-samples take the CCF value of corresponding mutations at A-sample.

Thus, somatic mutations in the A-sample and in the 16 M-samples were used to generate a tumor developmental tree (FIG. 8).

EXAMPLE 2

Quantitative Interpretation of Growth Advantageous Mutations in Cancer Subpopulations Based Upon a Tumor Developmental Tree A tumor developmental history in the form of a developmental tree shows the history of cancer cells dividing to produce their next generation (FIG. 8). Letters, such as, A and B, are used to represent any unique mutations. The number following a letter estimates the size of descendants. The tumor developmental tree is expressed as a rooted and bifurcated tree with nodes and edges. Somatic mutations are located at the nodes and edges.

Step 1. Interpretation of the tumor developmental history. According to the tree, "A" mutation originally occurs at a cell producing 100% of cancer cell population in the A-sample. The cell where "A" mutation initially occur produces two cells that are ancestors of two subpopulations with 66% and 34% of total populations and mutations "B" and "C" originally occur.

Step 2. A mutation's CCF value indicates the percentage of cancer cells carrying the mutation. Its location in a node specifies a progenitor cell that is the most recent ancestor cell for all cancer cells carrying the mutation.

Step 3. The location of a mutation in a developmental tree indicates if a mutation is common or exclusive to another mutation in cancer cell subpopulations. For instance, the cells with "B" and "C" mutations are mutually exclusive. Mutation "A" is common to all cancer cells. Mutation "B" is common to all cells that carry mutation "D" or "E".

Step 4. Driver mutations are non-synonymous somatic mutations in Cancer Gene Census database.

Quantitative interpretation of driver mutations in a tumor has implication in design of targeted therapy. For instance, targeting B or C may not bring control of tumor growth since either of them present in only portion of cancer cell population, 66% and 34%, respectively. Although targeting B may be more effective than targeting C alone, design of cocktail therapy targeting both driver mutations could potentially be more effective than the use of a single agent.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of acquiring specimens that are representative of a tumor in a patient comprising:
   (a) obtaining biological samples from the patient, wherein the samples include:
     a sample of a tumor mass,
     (ii) a sample from non-cancerous tissue;
   (b) randomly collecting two or more micro-samples (M-samples) from the tumor mass of step (a)(i), wherein each M-sample comprises two to 100 cells that are clonally related; and
   (c) converting the tumor mass of step (a)(i) remaining after the two or more M-samples are collected in step (b) into an aggregate sample (A-sample).

2. The method of claim 1, wherein the two or more M-samples are collected from an individual tumor mass or from a fine needle biopsy.

3. The method of claim 1, wherein the sample of a tumor mass is from fresh tissue, a snap frozen sample, or a formalin-fixed paraffin embedded specimen.

4. The method of claim 1, wherein the tumor is a primary tumor or part of the primary tumor.

5. The method of claim 1, wherein the tumor is a metastatic tumor or part of the metastatic tumor.

6. The method of claim 1, wherein the tumor is a solid tumor.

7. The method of claim 6, wherein the solid tumor is a breast, colon, lung, or prostate cancer.

8. The method of claim 1, wherein the non-cancerous tissue is non-cancerous tissue from the same patient.

9. The method of claim 8, wherein the non-cancerous tissue is blood, normal tissue adjacent to the tumor, or tissue from a different organ in the patient.

10. The method of claim 1, wherein DNA from the two or more M-samples is individually amplified by means of whole genome amplification.

11. The method of claim 1, further comprising (d) extracting DNA from the A-sample, and DNA from the non-cancerous tissue sample.

12. The method of claim 11, further comprising (e) barcoding the DNA from the A-sample and the DNA from the non-cancerous tissue sample.

13. The method of claim 12, comprising amplifying DNA from each M-sample by means of whole genome amplification, and further comprising (f) exon capturing the barcoded DNA from the A-sample, the barcoded DNA from the non-cancerous tissue, and the barcoded DNA from the two or more M-samples.

14. The method of claim 13, further comprising (g) performing next generation sequencing of the A-sample, of the non-cancerous tissue sample, and of the two or more M-samples to generate DNA sequencing data for the A-sample, the non-cancerous tissue sample, and the two or more M-samples.

15. The method of claim 1, wherein the two or more M-samples are obtained from the tumor by mass laser captured microdissection of a small clone of cells.

* * * * *